United States Patent
Roorda (10) Patent No.: US 7,481,790 B2
(45) Date of Patent: Jan. 27, 2009

(54) VESSEL ENLARGEMENT BY ARTERIOGENIC FACTOR DELIVERY

(75) Inventor: Wouter Roorda, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 747 days.

(21) Appl. No.: 09/749,144

(22) Filed: Dec. 27, 2000

(65) Prior Publication Data

US 2002/0103456 A1 Aug. 1, 2002

(51) Int. Cl.
*A61M 29/00* (2006.01)
(52) U.S. Cl. .................... 604/103.08; 604/60
(58) Field of Classification Search ........... 604/96, 604/103.08; 424/423, 130.1; 544/122; 530/388.23, 530/388.73
See application file for complete search history.

(56) References Cited

U.S. PATENT DOCUMENTS

| | | | |
|---|---|---|---|
| 3,978,055 A * | 8/1976 | Fauran et al. | ............ 544/122 |
| 4,465,669 A | 8/1984 | Wissler et al. | |
| 4,708,718 A | 11/1987 | Daniels | |
| 4,994,033 A | 2/1991 | Shockey et al. | |
| 5,059,211 A | 10/1991 | Stack et al. | |
| 5,087,244 A | 2/1992 | Wolinsky et al. | |
| 5,102,402 A | 4/1992 | Dror et al. | |
| 5,151,100 A | 9/1992 | Abele et al. | |
| 5,180,366 A | 1/1993 | Woods | |
| 5,232,444 A | 8/1993 | Just et al. | |
| 5,304,120 A | 4/1994 | Crandell et al. | |
| 5,304,121 A | 4/1994 | Sahatjian | |
| 5,306,286 A | 4/1994 | Stack et al. | |
| 5,324,261 A | 6/1994 | Amundson et al. | |
| 5,354,279 A | 10/1994 | Hofling | |
| 5,356,388 A | 10/1994 | Sepetka et al. | |
| 5,370,614 A | 12/1994 | Amundson et al. | |
| 5,380,307 A | 1/1995 | Chee et al. | |
| 5,380,747 A | 1/1995 | Medford et al. | |
| 5,397,307 A | 3/1995 | Goodin | |
| 5,415,636 A | 5/1995 | Forman | |
| 5,419,777 A | 5/1995 | Hofling | |
| 5,443,458 A | 8/1995 | Eury | |
| 5,462,523 A | 10/1995 | Samson et al. | |
| 5,464,395 A | 11/1995 | Faxon et al. | |
| 5,496,311 A | 3/1996 | Abele et al. | |

(Continued)

FOREIGN PATENT DOCUMENTS

EP 0 383 429 A2 8/1990

(Continued)

OTHER PUBLICATIONS

Rahimtoola S. "The Hibernating Myocardium", Am. Heart Journal, 1989, pp. 211-221, vol. 117, No. 1.

(Continued)

*Primary Examiner*—Stephen K. Cronin
(74) *Attorney, Agent, or Firm*—Blakely Sokoloff Taylor & Zafman LLP (57) ABSTRACT

A method of delivering an arteriogenic factor. The factor is delivered in a medically effective manner to structurally enlarge an existing blood vessel. A distal portion of a catheter can be advanced to an existing blood vessel to deliver the arteriogenic factor.

15 Claims, 4 Drawing Sheets

U.S. PATENT DOCUMENTS

| | | | |
|---|---|---|---|
| 5,514,092 | A | 5/1996 | Forman et al. |
| 5,527,337 | A | 6/1996 | Stack et al. |
| 5,538,504 | A * | 7/1996 | Linden et al. ............... 604/508 |
| 5,554,119 | A | 9/1996 | Harrison et al. |
| 5,558,642 | A | 9/1996 | Schweich, Jr. et al. |
| 5,569,197 | A | 10/1996 | Helmus et al. |
| 5,588,962 | A | 12/1996 | Nicholas et al. |
| 5,605,696 | A | 2/1997 | Eury et al. |
| 5,629,077 | A | 5/1997 | Turnlund et al. |
| 5,652,059 | A | 7/1997 | Margel |
| 5,661,133 | A | 8/1997 | Leiden et al. |
| 5,674,192 | A | 10/1997 | Sahatjian et al. |
| 5,693,029 | A | 12/1997 | Leonhardt |
| 5,713,860 | A * | 2/1998 | Kaplan et al. .......... 604/103.01 |
| 5,746,716 | A | 5/1998 | Vigil et al. |
| 5,753,504 | A * | 5/1998 | Kirkland et al. ............. 435/340 |
| 5,766,710 | A | 6/1998 | Turnlund et al. |
| 5,770,222 | A | 6/1998 | Unger et al. |
| 5,772,632 | A | 6/1998 | Forman |
| 5,792,094 | A | 8/1998 | Stevens et al. |
| 5,792,105 | A | 8/1998 | Lin et al. |
| 5,792,106 | A * | 8/1998 | Mische .................... 604/103.1 |
| 5,795,318 | A | 8/1998 | Wang et al. |
| 5,797,870 | A | 8/1998 | March et al. |
| 5,843,033 | A | 12/1998 | Ropiak |
| 5,843,051 | A | 12/1998 | Adams et al. |
| 5,852,175 | A | 12/1998 | Cummings et al. |
| 5,860,954 | A | 1/1999 | Ropiak |
| 5,866,561 | A | 2/1999 | Ungs |
| 5,868,719 | A | 2/1999 | Tsukernik |
| 5,877,295 | A * | 3/1999 | Diamond et al. ....... 530/388.73 |
| 5,879,713 | A | 3/1999 | Roth et al. |
| 5,893,840 | A | 4/1999 | Hull et al. |
| 5,941,868 | A | 8/1999 | Kaplan et al. |
| 5,951,458 | A | 9/1999 | Hastings et al. |
| 5,954,706 | A | 9/1999 | Sahatjian |
| 5,959,087 | A * | 9/1999 | Rathjen et al. ......... 530/388.23 |
| 5,985,307 | A * | 11/1999 | Hanson et al. ............... 424/423 |
| 6,013,099 | A | 1/2000 | Dinh et al. |
| 6,019,969 | A | 2/2000 | Cerami et al. |
| 6,048,332 | A * | 4/2000 | Duffy et al. ............. 604/103.08 |
| 6,123,939 | A * | 9/2000 | Shawver et al. .......... 424/130.1 |
| 6,169,077 | B1 | 1/2001 | Oehrlein |
| 6,283,947 | B1 | 9/2001 | Mirzaee |

FOREIGN PATENT DOCUMENTS

| | | |
|---|---|---|
| WO | WO96/39830 A1 | 12/1996 |
| WO | WO97/23256 A1 | 7/1997 |
| WO | WO99/49773 A2 | 10/1999 |

OTHER PUBLICATIONS

Chilian W. et al., "Microvascular Occlusions Promote Coronary Collateral Growth", Am. J Physiol, 1990, pp. H1103-H1111.

Schaper W., "Angiogenesis In The Adult Heart" Basic Res Cardiol, 1991, pp. 51-56, vol. 86 Suppl.

Riessen R. et al., "Prospects for Site-Specific Delivery of Pharmacologic and Molecular Therapies" JACC, Apr. 1994, pp. 1234-1244, vol. 23, No. 5.

Kersten J. et al., "Modulation of Coronary Collateral Angiogenesis: A Canine Model of Neovascularization Induced by Chronic Ischemia", J Card Surg, 1995, pp. 354-357, vol. 10.

Schaper W. et al., "Molecular Mechanisms of Coronary Collateral Vessel Growth", Circulation Research, Nov. 1996, pp. 911-919, vol. 79, No. 5.

Brieger D. et al., "Local Drug Delivery Systems And Prevention Of Restenosis", Cardiovascular Research, 1997, pp. 405-413, vol. 35.

Ito W. et al., "Angiogenesis But Not Collateral Growth is Associated With Ischemia After Femoral Artery Occlusion", Am. J. Physiol., 1997, pp. H1255-H1265, vol. 273.

Tyagi S., "Vasculogenesis and Angiogenesis: Extracellular Matrix Remodeling in Coronary Collateral Arteries and the Ischemic Heart", Journal of Cellular Biochemistry, 1997, pp. 388-394, vol. 65.

Saunders M. et al., "Release of Granulocyte-Macrophage Colony Stimulating Factor by Human Cultured Airway Smooth Muscle Cells: Suppression by Dexamethosone", Br J Pharmacol, Feb. 1997, pp. 545-546, vol. 120, No. 4.

Ito W. et al., "Monocyte Chemotactic Protein-1 Increases Collateral and Peripheral Conductance After Femoral Artery Occulsion", Circ Res, Jun. 1997, pp. 829-837, vol. 80, No. 6.

Weihrauch D. et al. "Repetitive Coronary Artery Occlusions Induce Release of Growth Factors into the Myocardial Interstitium", Am. J. Physiol, 1998, pp. H969-H976.

Wolf C. et al., "Vascular Remodeling and Altered Protein Expression During Growth of Coronary Collateral Arteries", J Mol. Cell. Cardiol., 1998, pp. 2291-2305, vol. 30, Academic Press.

Arras M. et al., "Monocyte Activation in Angiogenesis and Collateral Growth in the Rabbit Hindlimb", Journal of Clinical Investigation, Jan. 1, 1998, pp. 40-50, vol. 101, No. 1.

Ito W. et al., "Collateral Artery Growth" Local Drug Delivery Meeting and Cardiovascular Course on Radiation & Molecular Strategies, Feb. 26-28, 1998, Geneva, Switzerland.

Deindl E. et al., "VEGF, An Important Angiogenic Factor is Not Involved in Arteriogenesis" Journal of Molecular Medicine, May 1998, pp. B24, P-85.

Deindl E. et al., "Arteriogenesis Is Not Mediated By VEGF", Journal of Molecular and Cellular Cardiology, Jun. 1998, pp. A127, #497, vol. 30, No. 6.

Gourdie R. et al., "Endothelin-Induced Conversion of Embryonic Heart Muscle Cells Into Impulse-Conducting Purkinje Fibers", Proc Natl Acad Sci USA, Jun. 9, 1998, pp. 6815-6818, vol. 95, No. 12.

Hofer I. et al., "MCP-1 Increases the Number of Collaterals and Capillaries in the Rabbit Hindlimb", Journal of Molecular and Cellular Cardiology, Jun. 1998, pp. A126, #495, vol. 30, No. 6.

Tereb D. et al., "In Vivo Model for Coronary Artery Studies", Journal of Molecular and Cellular Cardiology, Jun. 1998, pp. A42, #157, vol. 30, No. 6.

Scheinowitz M. et al., "Fragmin Does Not Affect Left Ventricular Perfusion And Function Following Acute Mi in Swine", Journal of Molecular and Cellular Cardiology, Jun. 1998, pp. A42, #158, vol. 30, No. 6.

Vosschulte R. et al., "Extracellular Proteolysis is Essential For Coronary Arteriogenesis", Journal of Molecular and Cellular Cardiology, Jun. 1998, pp. A42, #159, vol. 30, No. 6.

Tsujimura s. et al., "Enhanced Expression of VEGF mRNA And Angiogenic Activity After Acute Myocardial Infarction (AMI) in Rats", Journal of Molecular and Cellular Cardiology, Jun. 1998, pp. A42, #160, vol. 30, No. 6.

Iwakura A. et al., "Coronary Stenosis and Mechanisms of Collateral Vessel Growth" Nippon Rinsho, Oct. 1998, pp. 2504-2508, vol. 56, No. 10.

Inoue M. et al., "Vascular Endothelial Growth Factor (VEGF) Expression in Human Coronary Atherosclerotic Lesions: Possible Pathophysiological Significance of VEGF in Progression of Atherosclerosis", Circulation, Nov. 17, 1998, pp. 2108-2116, vol. 98, No. 20.

Buschmann I. et al., "Attraction of Loaded Monocytes Via MCP-1: A Novel Strategy For Therapeutic Arteriogenesis", Oral Presentations: Max Planck Institute, Dept. for Experimental Cardiology, 1999.

www.naturalbypass.com, *Vasomedical, Inc.*, Dec. 3, 1999.

Soran O. et al., "Enhanced External Counterpulsation in the Management of patients with Cardiovascular Disease", Clin Cardiol, 1999, pp. 173-178, vol. 22.

Voelckel W. et al., "Effect of small dose dopamine on mesenteric blood flow and renal function in a pig model of cardiopulmonary resuscitation with vasopressin", Anesth Analg, 1999, pp. 1430-1436, vol. 89.

Macris M. et al., "Minimally Invasive Access of the Normal Pericardium: Initial Clinical Experience With a Novel Device", Clin Cardiol, Jan. 1999, pp. 136-139, vol. 1 Suppl 1.

Fleisch M. et al., "Direct Relation Between Quantitatively Determined Coronary Collateral Flow and Intracornary Basic Fibroblast Growth Factor Concentration", Oral Presentation: Session—Basic Aspects of Gene Therapy and Angiogenesis, Morial Convention Center, Room 222, Mar. 9, 1999, Abstract 826-5.

Gibson M. et al., "Magnitude and Location of New Angiographically Apparent Coronary Collaterals Following Intravenous VEGF Administration", Oral Presentation: Session—Intractable Angina: Trials of Vascular Growth Factors, Morial Convention Center, Room 345, Mar. 10, 1999, Abstract 874-5.

Isner J. et al., "Angiogenesis and Vasculogenesis as Therapeutic Strategies for Postnatal Neovascularization", The Journal of Clinical Investigation, May 1999, pp. 1231-1236, vol. 103, No. 9.

Buschmann I. et al., "Arteriogenesis Versus Angiogenesis: Two Mechanisms of Vessel Growth" News Physiol. Sci., Jun. 1999, pp. 121-125, vol. 14.

Ito K. et al., "Impact of Coronary Artery Remodeling On Misinterpretation of Angiographic Disease Eccentricity: Evidence From Intravascular Ultrasound" Int J Cardiol, Aug. 31, 1999, pp. 275-282, vol. 70, No. 3.

Taylor A. et al., "Arterial Remodeling in the Left Coronary System: the Role of High-Density Liproprotein Cholesterol", J Am Coll Cardiol, Sep. 1999, pp. 760-767, vol. 34, No. 3.

Fussl R. et al., "Type and Extent of Vascular Remodeling in Significant Coronary Lesions: An Intravascular Ultrasound Study", Z Kardiol, Oct. 1999, pp. 780-787, vol. 88, No. 10.

Ignatescu M. et al., "Expression of the Angiogenic Protein, Platelet-Derived Endothelial Cell Growth Factor, in Coronary Atherosclerotic Plaques: In Vivo Correlation of Lesional Microvessel Density and Constrictive Vascular Remodeling", Aterioscler Thromb Vasc Biol, Oct. 1999, pp. 2340-2347, vol. 19, No. 10.

Fleisch M. et al., "Physiologically Assessed Coronary Collateral Flow and Intracoronary Growth Factor Concentrations in Patients With 1- to 3-Vessel Coronary Artery Disease", Circulation, Nov. 9, 1999, pp. 1945-1950.

PCT International Search Report for PCT Appln No. US01/32386, mailed May 3, 2002 (7 pages).

PCT Written Opinion for PCT International Appln No. US01/32386, mailed Jun. 19, 2003 (6 pages).

* cited by examiner

VESSEL ENLARGEMENT BY ARTERIOGENIC FACTOR DELIVERY

BACKGROUND OF THE INVENTION

The present invention relates to induction of vessel enlargement. In particular, the present invention involves delivery of arteriogenic factors to cause structural enlargement of existing blood vessels.

BACKGROUND OF THE PRIOR ART

Coronary and peripheral arteries are naturally susceptible to atherosclerotic blockages (i.e. stenotic lesions). Both genetic and environmental factors play a role in the occurrence of atherosclerosis. The presence of an atherosclerotic blockage hampers circulation by occlusion of the affected vessel with plaque and smooth muscle cell build up. In the case of coronary arteries, such occlusions can lead to heart attacks and are potentially fatal. Impaired circulation in peripheral arteries is also accompanied with health risk.

Fortunately, the body is equipped with a natural defense mechanism, arteriogenesis, to help combat the effects of atherosclerosis. Arteriogenesis is the proliferative enlargement of pre-existing small collateral arteries, arterioles, or capillaries. For example, collateral arteries may branch off of an occluded larger artery near an occluded portion of the larger artery, thereby providing a natural bypass. This bypass is an alternative pathway for blood flow to that provided by the occluded larger artery. This alternative pathway (i.e. the collateral arteries) may naturally grow in response to the presence of the occlusion in the larger artery. Growth of such collateral arteries in this manner is generally known as arteriogenesis. Arteriogenesis may act in this manner to increase the size of the bypass and compensate for the decrease in circulation through the occluded artery.

Unfortunately, naturally occurring arteriogenesis is not always enough to compensate for the decrease in circulation through an occluded artery. In many cases, the rate and extent of occlusion build up is much greater than the body's ability to compensate with natural arteriogenesis. Where natural arteriogenesis is not enough to compensate for compromised circulation, medical intervention is required. Minimally invasive surgical procedures or more direct surgical bypass procedures (i.e. open heart surgery) may be required. These procedures may be coronary or peripheral, such as where treatment or bypass of the superficial femoral artery (SFA) is desired.

Minimally invasive procedures such as percutaneous transluminal coronary angioplasty (PTCA) are widely utilized. A PTCA procedure involves the insertion of an angioplasty balloon at the distal end of a catheter to the site of a stenotic lesion or occlusion in the larger artery. Once advanced, the balloon is inflated compressing the stenosis and widening the lumen in order to allow an efficient flow of blood through the lumen. Often, PTCA is followed by stent delivery to the site of the former stenosis. A stent is a tubular structure which provides support to the once narrowed artery to help maintain the now present widened state of the artery.

More direct bypass procedures, such as open heart surgery, are more traumatic for the patient but may be necessary where, for example, a PTCA procedure fails to have a more permanent vessel widening effect. The more traditional open heart surgical bypass requires the opening of the patient's chest cavity and the direct manipulation and grafting of vessel configurations to create a bypass around an occluded artery. Rehabilitation from such procedures is longer and more difficult for the patient.

Unfortunately, the success rate and availability of surgical intervention alone is limited. That is, in some cases neither invasive nor minimally invasive procedures, as described above, are available to the patient as a treatment option. This is because minimally invasive treatment can fail to have a more permanent vessel widening effect as described above and due to the fact that many patients are not viable candidates for more invasive procedures. For example, a patient may be a diabetic with limited access for a minimally invasive surgical option, or unable to undergo the trauma associated with a more direct invasive bypass procedure as discussed above. Such a patient would not be a candidate for either the invasive or minimally invasive procedures discussed above. Therefore, what is desired is a method of delivering an arteriogenic factor to structurally enlarge an existing blood vessel.

SUMMARY OF THE INVENTION

An embodiment of the present invention provides a method of delivering an arteriogenic factor. The factor is delivered in a medically effective manner to structurally enlarge an existing blood vessel.

A method embodiment of structurally enlarging an existing blood vessel is provided where a distal portion of a catheter is advanced to an existing blood vessel. An arteriogenic factor is delivered to the existing blood vessel via said catheter in a medically effective manner.

In another embodiment of the invention an apparatus which includes an elongated catheter body having a distal portion is provided. The distal portion of the catheter is configured to deliver an arteriogenic factor to a vessel region in a medically effective manner to structurally enlarge an existing blood vessel.

DETAILED DESCRIPTION OF THE INVENTION

While the background of the present invention is described with reference to certain methods of inducing arteriogenesis and devices, agents and other materials therefore, the invention is applicable to any medically effective induction of arteriogenesis. While the description makes reference to numerous specific details in order to provide a thorough understanding of the present invention, each specific detail need not be employed to practice the present invention. Additionally, well-known details, such as particular materials or methods, have not been described in order to avoid obscuring the present invention.

Figure 1:
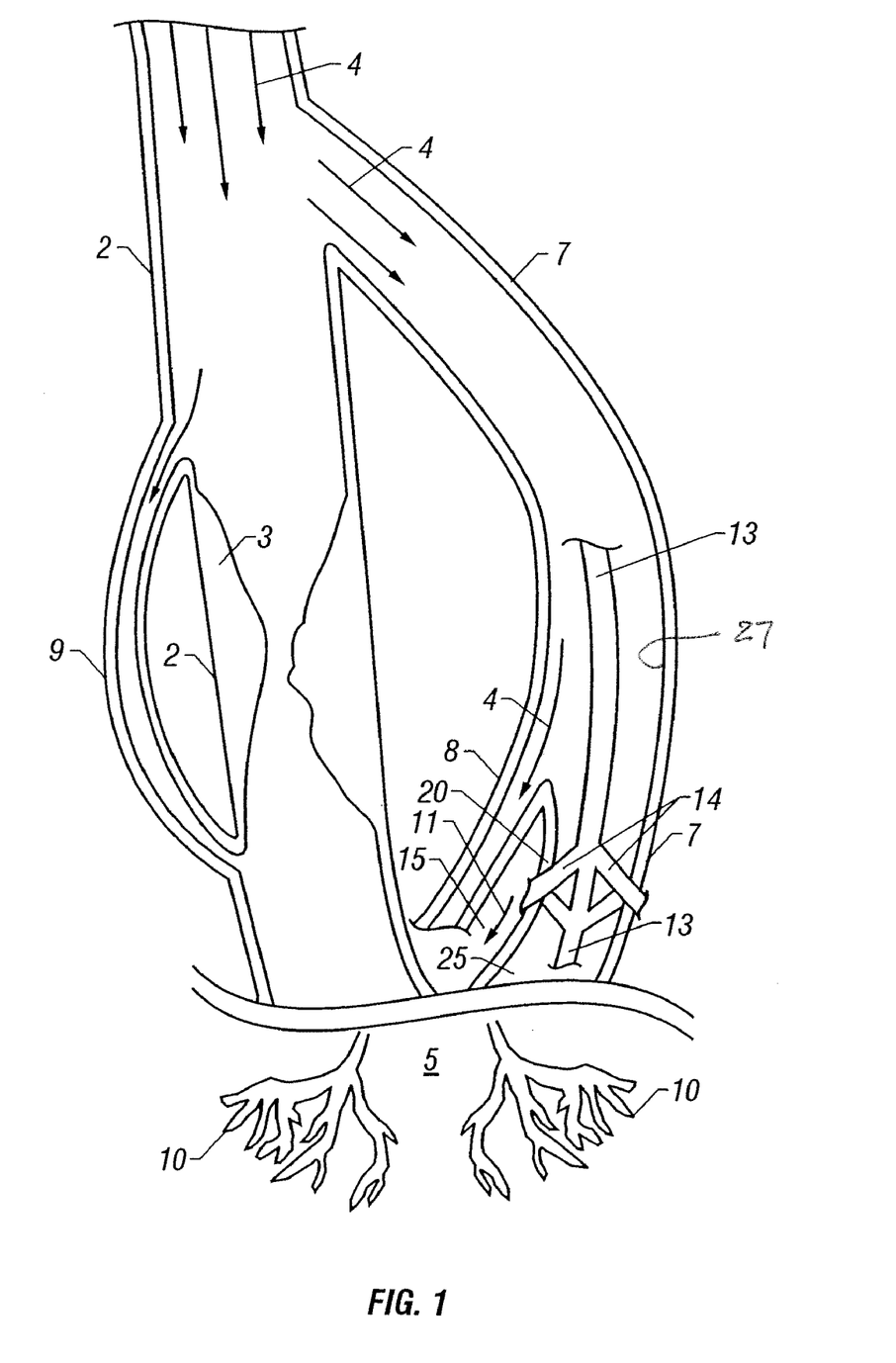
FIG. 1 is a cross sectional view of a vessel receiving extravascular treatment with an arteriogenic factor.
Figure 2:
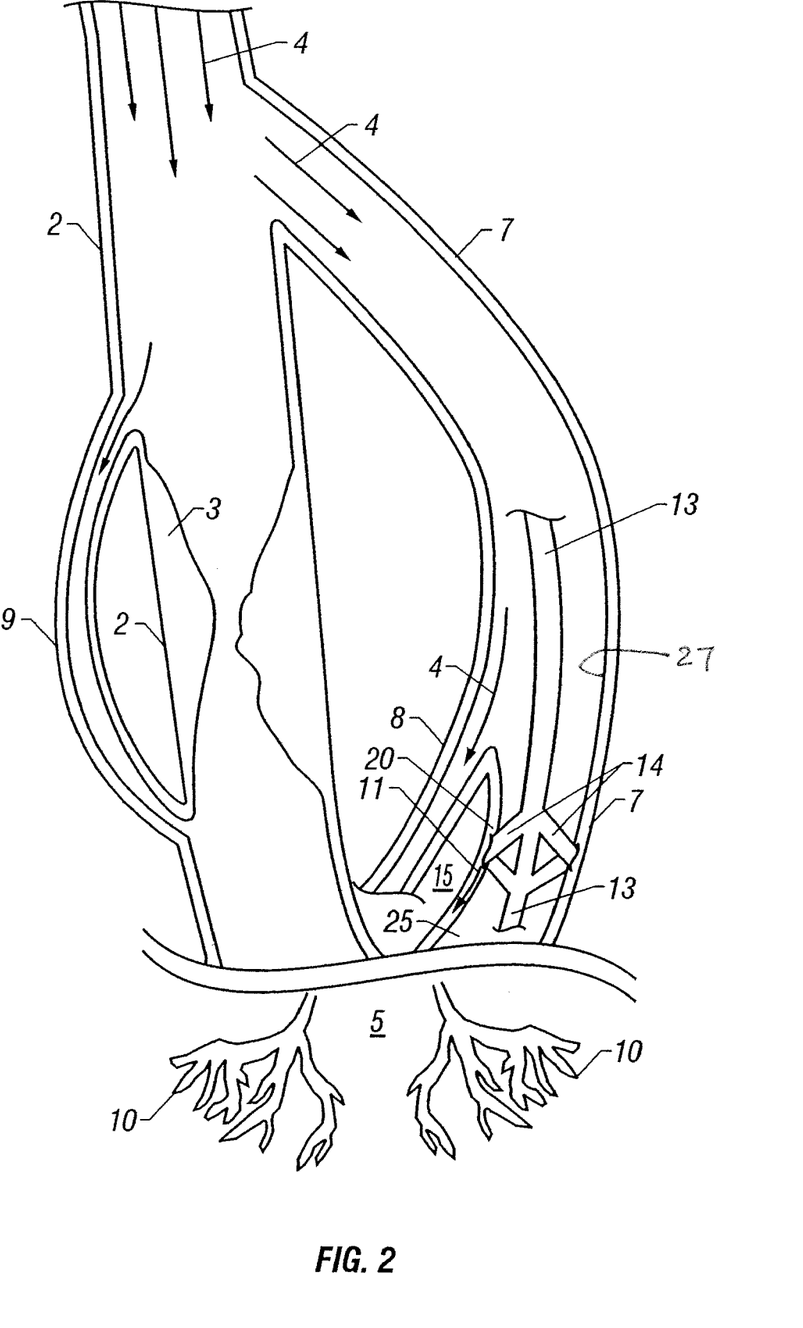
FIG. 2 is a cross sectional view of a vessel receiving intramural treatment with an arteriogenic factor.

With reference to FIGS. 1 and 2, embodiments of the present invention are shown. A primary vessel 2 is shown which is intended to deliver a flow of blood 4 to a target area 5, such as myocardium, by way of capillaries 10. However, the primary vessel 2 is impaired with an occlusion 3 such as a stenotic lesion. Such an occlusion 3 is often indicative of potentially widespread atherosclerosis. The occlusion 3 limits the flow of blood 4 through the primary vessel 2, thus, decreasing circulation and limiting the flow of blood 4 able to reach the target area 5.

In addition to the primary vessel 2, smaller bypass vessels 7, 8, 9 are present which provide a path for delivery of the flow of blood 4 to the target area 5. The bypass vessels 7, 8, 9 include a side branch 7, a tertiary branch 8, and a looping branch 9. The bypass vessels 7, 8, 9 allow a manner of collateral circulation which can involve independent pathways to the target area 5. Alternatively, the bypass vessels 7, 8, 9 can provide a manner of bypassing the occlusion 3 and redelivering a flow of blood 4 to the primary vessel 2 as a means of providing access to the target area 5. Additionally, the bypass vessels 7, 8, 9 may have been angiogenically induced and not originally present prior to angiogenesis. Irrespective of prior angiogenic induction it is desirable to ensure the ability of a bypass vessel 7, 8, 9 to direct a flow of blood 4 to the target area 5. Thus, arteriogenesis is still desired.

The side branch 7 emanates from the primary vessel 2 at a particular position. This position is such that the flow of blood 4 has access to the side branch 7 prior to encountering the occlusion 3. The side branch 7 provides access to the target area 5 generally. Therefore, the flow of blood 4 which passes through the side branch 7 bypasses the occlusion 3 in order to reach the target area 5.

The tertiary branch 8 emanates from the side branch 7. The tertiary branch 8 provides access to the target area 5 generally and, in an alternate vessel configuration, can connect to the primary vessel 2 at a post occlusion position (not shown). The post occlusion position is such that where the flow of blood 4 travels through the tertiary branch 8, it bypasses the occlusion 3 in order to regain access to the primary vessel 2. Thus, the target area 5 is still provided with circulation via the primary vessel 2.

A looping branch 9 is shown emanating from the primary vessel 2 and terminating at the primary vessel 2. The looping branch 9 emanates and terminates with respect to the primary vessel 2 in a manner which provides a complete alternate route for a portion of the flow of blood 4 to bypass the occlusion 3. This bypass is similar to the tertiary branch 8 bypass in situations where the tertiary branch 8 connects to the primary vessel 2 at a post occlusion position. That is, the flow of blood 4 is provided access back to the primary vessel 2 in order to reach the target area 5.

Although the bypass vessels 7, 8, 9 provide an alternate means of access to the target area 5, they are initially relatively small vessels in comparison to the primary vessel 2. Therefore, the bypass vessels 7, 8, 9 are not initially able to completely compensate for the lack of circulation provided to the target area 5 as a result of the occlusion 3. Therefore, in embodiments of the invention, treatment with an arteriogenic factor is introduced to increase the size of the bypass vessels 7, 8, 9. Increasing the size of the bypass vessels 7, 8, 9 allows for a more complete compensation for the lack of circulation provided through the primary vessel 2 as a result of the occlusion 3. For purposes of illustration, the vessel configuration of FIGS. 1-4 are shown. However, in embodiments of the invention the following methods of encouraging arteriogenesis can be applied to any situation or vessel configuration where a target area 5 is receiving a less than desired blood supply and there is a desire to structurally enlarge a vessel which, prior thereto, supplies the target area 5 with the less than desired blood supply.

In embodiments of the invention, delivery of an arteriogenic factor to a vessel region is used to encourage arteriogenesis thereat. The induction of arteriogenesis includes an actual structural enlargement of the vessel involved (i.e. as opposed to a more temporary dilation). The arteriogenesis is induced in a medically effective manner in terms of delivery, dosage, and formulation of the arteriogenic factor.

By way of example, embodiments of inducing arteriogenesis are described here with reference to the side branch 7. However, in alternative embodiments arteriogenesis is induced as described herein to any vessel shown, including the tertiary branch 8, the looping branch 9, or the primary vessel 2 itself. Additionally, in other alternative embodiments, treatment is enhanced by combining the types of arteriogenic factors which are delivered.

As shown in FIGS. 1 and 2, a needle catheter 13 is advanced to the side branch 7. The needle catheter 13 delivers arteriogenic factor to act upon and induce arteriogenesis of the side branch 7.

The arteriogenic factor delivered in the embodiments of FIGS. 1 and 2 is an arteriogenic chemical factor 11, such as a chemical, drug, protein, or gene construct. A gene construct will include a gene vector or naked DNA which encodes for a desired protein or agent that enhances an arteriogenic response by the side branch 7.

Arteriogenic chemical factors 11 delivered in embodiments of the invention include inflammatories. That is, inflammatories, which can enhance any of a cascade of inflammatory events, are often likely to lead to arteriogenesis due to a vessel's natural inflammatory response mechanism. Inflammatories which act as arteriogenic chemical factors 11 include naturally occurring classic mediators, blood-borne molecules, and cell-bound molecules.

Classic mediators include histamine and bradykinin. Blood-borne molecules that promote the recruitment of inflammatory cells include Complement Factor 5A, Platelet Activating Factor (PAF), prostaglandins, leukotrienes (such as leukotriene B4 (LTB4)), cytokines, (such as Interleukin 1 (IL-1) and Tumor Necrosis Factor (TNF)), and Monocyte Chemoattractant Protein (MCP-1). Cell-bound molecules include Intracellular Adhesion Molecules (ICAM's), Vascular Cell Adhesion Molecules (VCAM's), E selectin, P selectin, L selectin, and leukocyte integrins.

Alternative inflammatory compounds which induce arteriogenesis include endotoxins such as bacterial endotoxins. Bacterial endotoxins are lipo-Guidant polysaccharides which promote inflammation. Heavy metal compounds such as iron or copper salts are used to induce an inflammatory response in alternative embodiments.

In another embodiment of the invention, an arteriogenic chemical factor 11 is introduced, such as NG-nitro L-arginine methyl ester (L-NAME) or asymmetric di-methyl arginine (ADME), which are not inflammatories. However, these particular factors increase the adhesive abilities of inflammatory cells. Additionally, Basic Fibroblast Growth Factor (B-FGF), which is also not an inflammatory, is used in an embodiment of the invention.

Delivery of an arteriogenic chemical factor 11 as described in the above embodiments can be in an amount of between about 0.01 nanogram and about 1 milligram per gram of tissue to be treated, with possible exception of the blood-borne molecules delivered intravascularly as discussed later herein. Additionally, embodiments of the invention include treatment with an immediate induction, while alternative embodiments include treatment over a predetermined duration of time (e.g. between about one and about five weeks). Treatment over a predetermined duration of time can be accomplished through several separate deliveries, preferably between about 3 and about 10 days apart from one another. In an alternative embodiment the administration of the arteriogenic chemical factor 11 is continuous by way of a controlled release.

In order to obtain a controlled release, the arteriogenic chemical factor 11 is incorporated with a performance enhancing additive in an embodiment of the invention. For example, the arteriogenic chemical factor 11 is suspended within, or as a part of, a microparticle to ensure treatment over a desired duration of time. The microparticle is a microsphere or microcapsule which is degradable at a designed rate. One such example is a polylactic acid membrane microparticle which contains the desired arteriogenic chemical factor 11. In another alternative embodiment, the arteriogenic chemical factor 11 is incorporated with a liposome to obtain a desired rate of degradation. Other alternative embodiments utilize stabilizers, agents such as buffers, anti-oxidants, and protease inhibitors, that increase the stability of the arteriogenic chemical factor which are combined with the arteriogenic chemical factor 11.

Continuing with reference to FIGS. 1 and 2, the needle catheter 13 is a catheter equipped with needles 14. The needles 14 deliver the arteriogenic chemical factor 11 to the vessel area.

Referring to FIG. 1, the vessel area to which the arteriogenic chemical factor 11 is delivered is an extravascular vessel area 15. That is, in the embodiment shown, it is desirable to induce arteriogenesis at a location that the side branch 7 does not yet occupy as a means of encouraging vascular growth outward toward that location.

Extravascular delivery is desirable where the vessel to undergo arteriogenesis is not readily accessible. For example, in an alternative embodiment, delivery of the arteriogenic chemical factor 11, by accessing the sizable side branch 7, is also used to effect arteriogenesis at the much smaller, and more difficult to access, tertiary branch 8. Delivery of arteriogenic chemical factor 11 to the extravascular vessel area 15, adjacent the tertiary branch 8, makes this possible. In other alternative embodiments, other extravascular vessel areas 15, such as within the pericardium generally, near the site of the occlusion 3, are treated in this manner to encourage arteriogenesis of the side branches 7, 8, 9 or the primary branch 2.

In other embodiments alternative devices are used to deliver the arteriogenic chemical factor 11. Catheters with specially designed drug delivery tips, syringes and other non-catheter devices are used to deliver the arteriogenic chemical factor 11 to the extravascular vessel area 15 in these alternative embodiments.

Referring to FIG. 2, another alternative embodiment of the present invention is shown. In this embodiment it is desirable to act within the vessel itself to more directly induce arteriogenesis upon the side branch 7. That is, to act upon the intramural vessel area 20. Again, a needle catheter 13 is used. However, in other embodiments catheters with specially designed drug delivery tips, syringes or other non-catheter devices are used to deliver the arteriogenic chemical factor 11 to the intramural vessel area 20. Where a needle catheter 13 is used, the needles 14 are extended only to within the intramural vessel area 20 to deliver the arteriogenic chemical factor 11.

Figure 3:
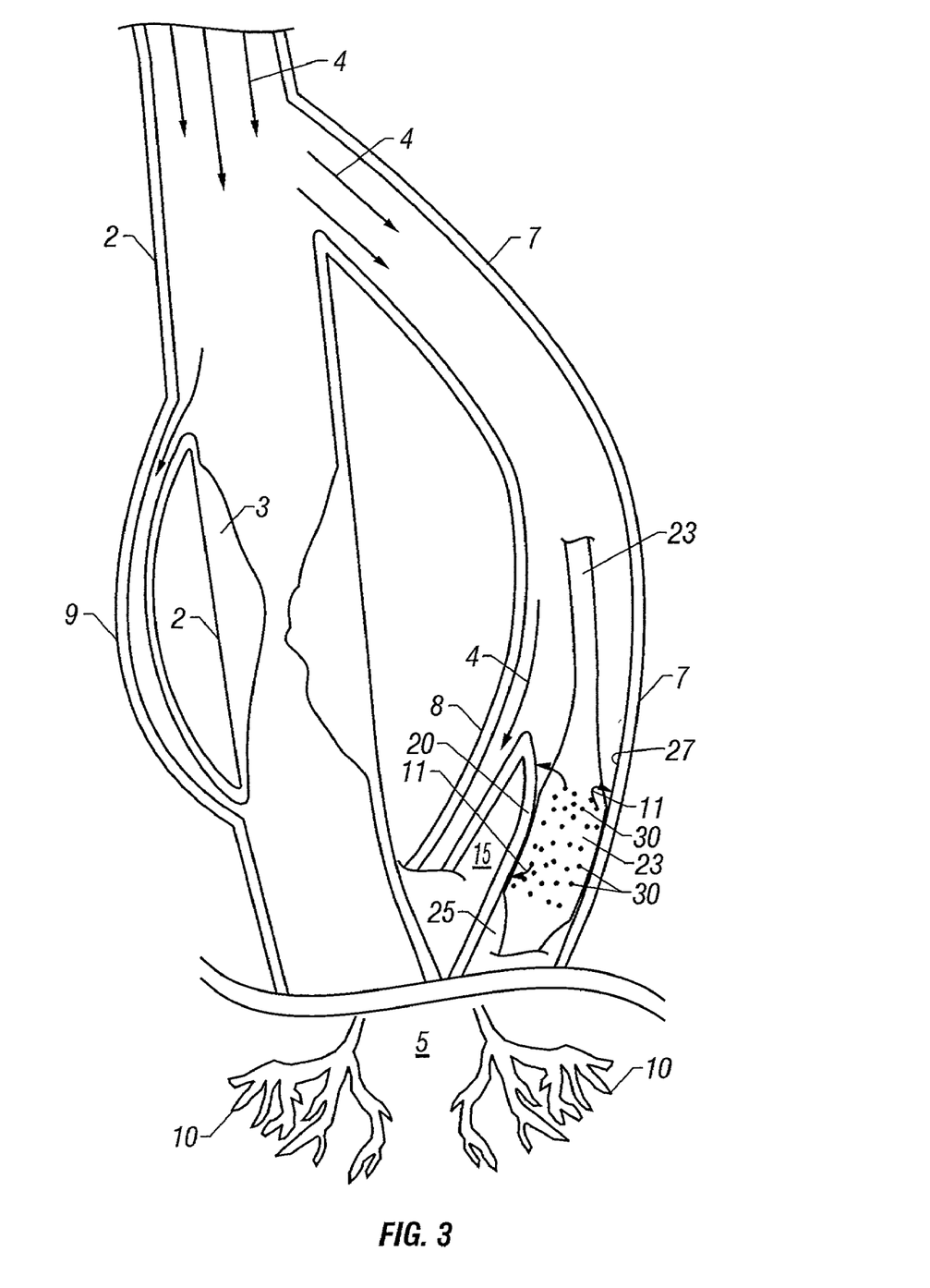
FIG. 3 is a cross sectional view of a vessel receiving intravascular treatment with an arteriogenic factor.

Referring to FIG. 3, an alternative embodiment of the invention is shown. In this embodiment a manner of delivering the arteriogenic chemical factor 11 intravascularly is shown. A porous balloon catheter 23 is used to deliver the arteriogenic chemical factor 11. Pores 30 are present which allow the porous balloon catheter 23 to release the arteriogenic chemical factor 11. The pores 30 are micropores if desired. A delivery as shown induces arteriogenesis by directing the arteriogenic chemical factor 11 at the vessel surface 27 which defines the intravascular vessel area 25. In one embodiment the delivery occurs slightly upstream of the portion of the vessel surface 27 to be treated with the understanding that the arteriogenic chemical factor 11 will migrate in the direction of the flow of blood 4.

In addition to the porous balloon catheter 23, other delivery devices are used in alternative embodiments to deliver the arteriogenic chemical factor 11 intravascularly. For example, in one embodiment a double balloon catheter, having occluding balloons spaced apart longitudinally, is used to deliver the arteriogenic chemical factor 11 between the occluding balloons. In another alternative embodiment, a stent loaded with an arteriogenic chemical factor 11 is implanted within the side branch. As with other vessel areas 15, 20, a catheter with a specially designed drug delivery tip, a syringe, or other non-catheter device is used to deliver the arteriogenic chemical factor 11 to the intravascular vessel area 25 in other embodiments. Additionally, in one embodiment the needle catheter 13 of FIGS. 1 and 2 is used for intravascular delivery where the needles 14 are extended only to within the intravascular vessel area 25.

Intravascular delivery of the arteriogenic chemical factor 11 is in an amount of between about 10 picograms to about 1 microgram per milliliter of blood (i.e. in the intravascular vessel area 25). Preferably, the arteriogenic chemical factor is a blood-borne molecule and the delivery occurs via a controlled and continuous release as described previously. However, the release need not be constant.

In addition to the more specific deliveries described above, in an alternative embodiment delivery is general and need not focus on a particular vessel area 15, 20, 25. Rather, delivery is directed generally into tissue and vasculature in an area of the occlusion 3, for example, by way of a syringe. Such a general delivery provides arteriogenic chemical factor 11 to one or more the vessel areas 15, 20, 25 simultaneously while also affecting multiple vessels 2, 7, 8, 9 simultaneously.

Alternative methods of introducing an arteriogenic physical factor are used in alternative embodiments. For example, in alternative embodiments catheters equipped with cutters or puncturing features, such as the needles 14 of FIGS. 1 and 2, are used to focus acute injury on any portion of the vessel area to induce an inflammatory response and thus, arteriogenesis. The injury is the result of minor shear or compressive stress applied to the vessel surface 27. In other embodiments these alternative devices are used to more directly effect injury beyond the vessel surface 27 and into the intramural vessel area 20 or the extravascular vessel area 15. For example, in one embodiment the needle catheter 13 of FIGS. 1 and 2 is used to injure the vessel surface 27 (defining the intravascular vessel area 25), the intramural vessel area 20, and the extravascular vessel area 15 simultaneously. This is because the needles 14 are advanced into the extravascular vessel area 15 from within the intravascular area 25, affecting all vessel areas 15, 20, 25.

In addition to the above referenced arteriogenic factors, alternative embodiments utilize other arteriogenic factors. For example, in one embodiment an arteriogenic thermal factor is introduced. An arteriogenic thermal factor is introduced, for example, by way of a cryocatheter, having a distal portion of between about 0° Celsius (C) and about 10° C., and more preferably between about 0° C. and about 4° C. The cryocatheter is briefly introduced to cause local injury to the vessel area making contact or close association with the distal portion of the cryocatheter. Alternatively, in another embodiment a heated catheter having a distal portion of between about 40° C. and about 99° C., is introduced. In either case, an arteriogenic thermal factor can be introduced to cause an inflammatory response and induce arteriogenesis.

Figure 4:
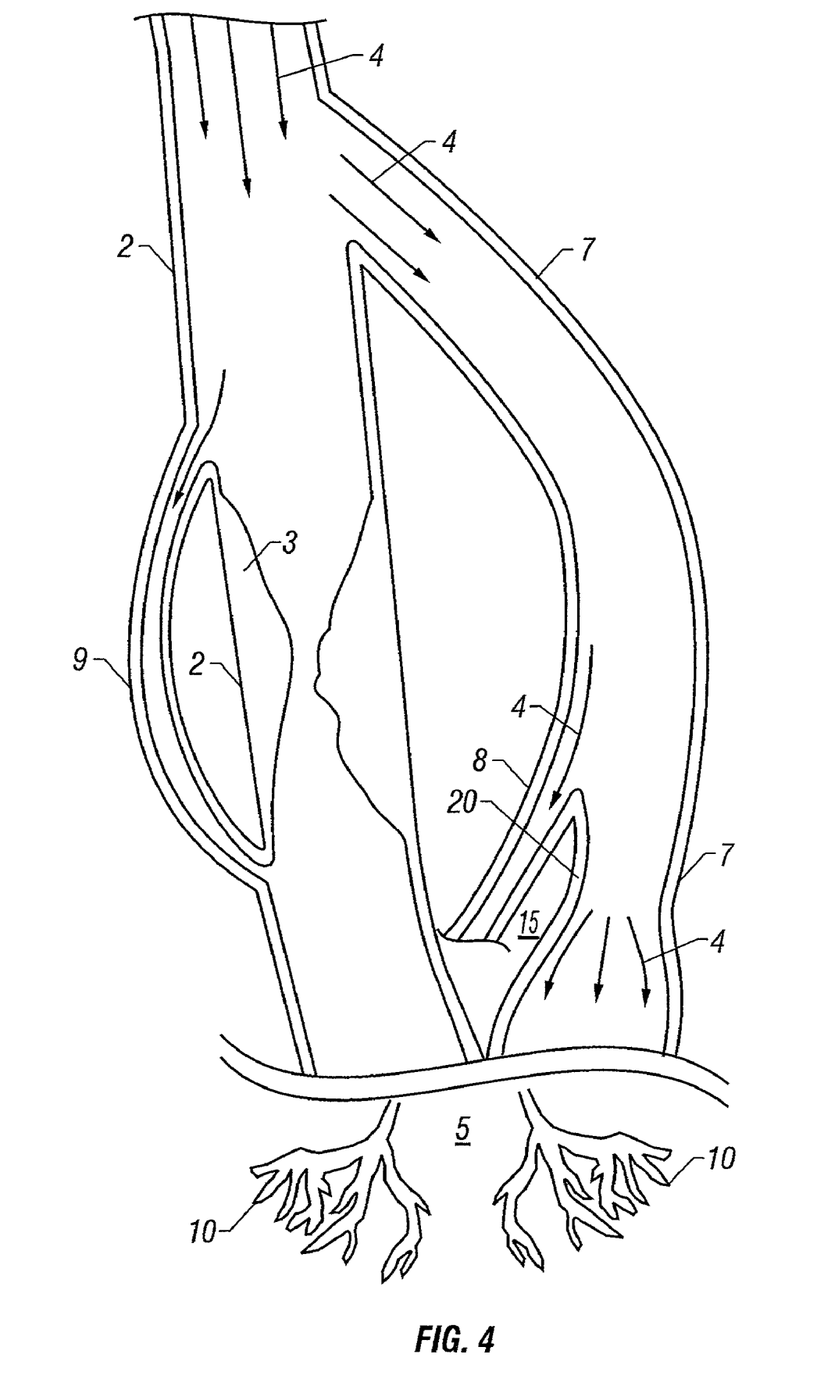
FIG. 4 is a cross sectional view of a vessel having received treatment with an arteriogenic factor.

Referring to FIG. 4, the side branch 7 is shown following application of an arteriogenic factor thereto. The side branch 7 has been widened where the arteriogenic factor has been introduced. This increases the flow of blood 4 through the side branch and helps to compensate for the occlusion 3 within the primary vessel 2. Treatment with an arteriogenic factor is continued throughout the remainder of the side branch 7 until the occlusion 3 is compensated for with an enlarged bypass provided through arteriogenesis. In alternative embodiments the remaining vessels 2, 8, 9 are enlarged through arteriogenesis as described herein.

Embodiments of the invention include manners of increasing the rate of arteriogenesis such that a natural bypass or vascular widening is enhanced. Additionally, embodiments of the invention can be employed in minimally invasive manners to avoid undue trauma to a patient that can be associated with more invasive procedures such as open-heart surgery.

Although exemplary embodiments of the invention describe particular methods of delivering arteriogenic agents to a vessel area, other methods of the invention including alternate methods of delivery can be utilized. Many changes, modifications, and substitutions maybe made without departing from the scope of this invention.

I claim
1. A method comprising:
  injuring a vessel region, the vessel region comprising a bypass vessel leading to a target area for blood flow, wherein the bypass vessel is adjacent to a primary vessel leading to the target area, the primary vessel having an occlusion to blood flow; and
  delivering an arteriogenic factor to the bypass vessel in a medically effective manner to structurally enlarge an existing blood vessel.

2. The method of claim 1 wherein delivering comprises providing the arteriogenic factor to the vessel region for a duration ranging from about one week to about five weeks.

3. The method of claim 1 further comprising providing a second delivery of the arteriogenic factor to the vessel region at about 3 to about 10 days after the delivering.

4. The method of claim 1 wherein delivering comprises:
  providing a syringe to accommodate the arteriogenic factor; and
  advancing the arteriogenic chemical factor from the syringe to the vessel region.

5. The method of claim 1 wherein delivering comprises:
  providing a needle catheter to accommodate the arteriogenic factor; and
  advancing the arteriogenic factor from the needle catheter to the vessel region.

6. The method of claim 1 wherein delivering comprises:
  providing a porous balloon catheter having a porous balloon to accommodate the arteriogenic factor; and
  advancing the arteriogenic factor from the porous balloon to the vessel region via pores of the porous balloon.

7. The method of claim 1 wherein the arteriogenic factor is a needle catheter, the delivery comprising advancing a needle of the needle catheter to the vessel region, the needle to puncture the vessel region.

8. The method of claim 1 wherein delivering the arteriogenic factor includes delivering a catheter with a distal portion cooled to between about 0° C. and about 10° C.

9. The method of claim 1 wherein delivering the arteriogenic factor includes delivering a catheter with a distal portion heated to a range from about 40° C. to about 90° C.

10. A method of structurally enlarging a bypass vessel adjacent to a primary vessel, the method comprising:
  injuring the bypass vessel, wherein the bypass vessel and a primary vessel provide a path for delivery to a target area and wherein the primary vessel comprises an occlusion;
  advancing a distal portion of a catheter to the bypass vessel;
  delivering an arteriogenic factor in a medically effective manner to the bypass vessel via the catheter; and
  causing an enlargement to at least a portion of the bypass vessel.

11. The method of claim 10 wherein delivering further comprises providing the arteriogenic factor to the bypass vessel for a duration ranging from about one week to about five weeks.

12. The method of claim 10 wherein delivering further comprises providing a second delivery of the arteriogenic factor to the bypass vessel at about 3 to about 10 days after a first delivering of the arteriogenic factor.

13. The method of claim 10 wherein delivering further comprises:
  providing a syringe to accommodate the arteriogenic factor; and
  advancing the arteriogenic factor from the syringe to the bypass vessel.

14. The method of claim 10 wherein delivering further comprises:
  providing a needle catheter to accommodate the arteriogenic factor; and
  advancing the arteriogenic factor from the needle catheter to the bypass vessel.

15. The method of claim 10 wherein delivering further comprises:
  providing a porous balloon catheter having a porous balloon to accommodate the arteriogenic factor; and
  advancing the arteriogenic factor from the porous balloon to the bypass vessel via pores of the porous balloon.

* * * * *